United States Patent [19]
Pettersen

[11] Patent Number: 6,013,056
[45] Date of Patent: Jan. 11, 2000

[54] SELF-DESTRUCTING INJECTION SYRINGE

[76] Inventor: Tor-Erling Pettersen, Lalienveien 1, N-1453 Bjørnemyr, Norway

[21] Appl. No.: 09/125,401
[22] PCT Filed: Feb. 5, 1997
[86] PCT No.: PCT/NO97/00032
§ 371 Date: Aug. 6, 1998
§ 102(e) Date: Aug. 6, 1998
[87] PCT Pub. No.: WO97/28836
PCT Pub. Date: Aug. 14, 1997

[30] Foreign Application Priority Data

Feb. 6, 1996 [NO] Norway ..................................... 960485

[51] Int. Cl.$^7$ ....................................................... A61M 5/00
[52] U.S. Cl. ........................................... 604/110; 604/228
[58] Field of Search .................................. 604/110, 187, 604/218, 228

[56] References Cited

U.S. PATENT DOCUMENTS

| 4,775,363 | 10/1988 | Sandsdalen | 604/110 |
| 4,908,020 | 3/1990 | Pettersen | 604/110 |
| 5,181,912 | 1/1993 | Hammett | 604/228 X |
| 5,643,211 | 7/1997 | Sadowski et al. | 604/110 |

Primary Examiner—John D. Yasko
Attorney, Agent, or Firm—Abelman, Frayne & Schwab

[57] ABSTRACT

A self-destructing hypodermic syringe (1) comprising an optionally graduated barrel (2) having a Luer lock-tip (13) in one end and a plunger head (5) with plunger rod (3), of the type which has a breaking element (4) incorporated in connection with the plunger head or plunger rod, and where the breaking element (4) is broken when the syringe (1) is used for the first time, wherein the breaking element (4), is cast in one piece with the plunger rod (3) and initially, prior to destruction, is secured thereto via diametrically arranged cam follower hoops (6) and lugs (7) which, when loaded, are broken at perforations (7') while converting the lugs (7) to cam followers (7).

1 Claim, 3 Drawing Sheets

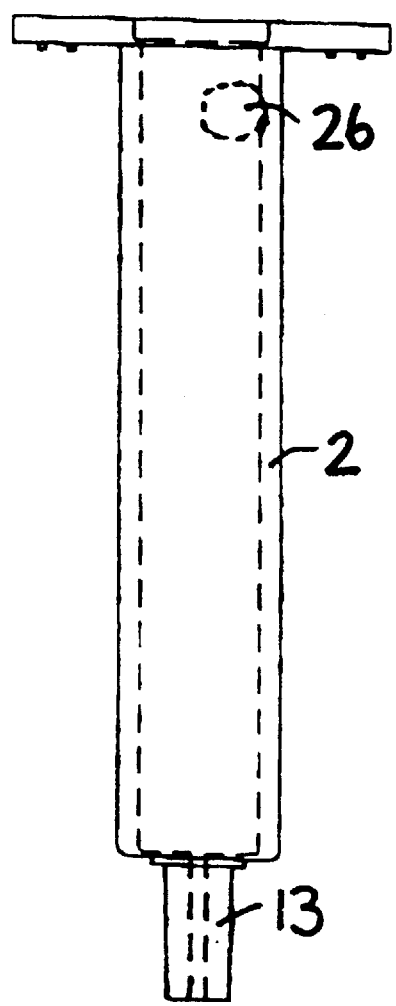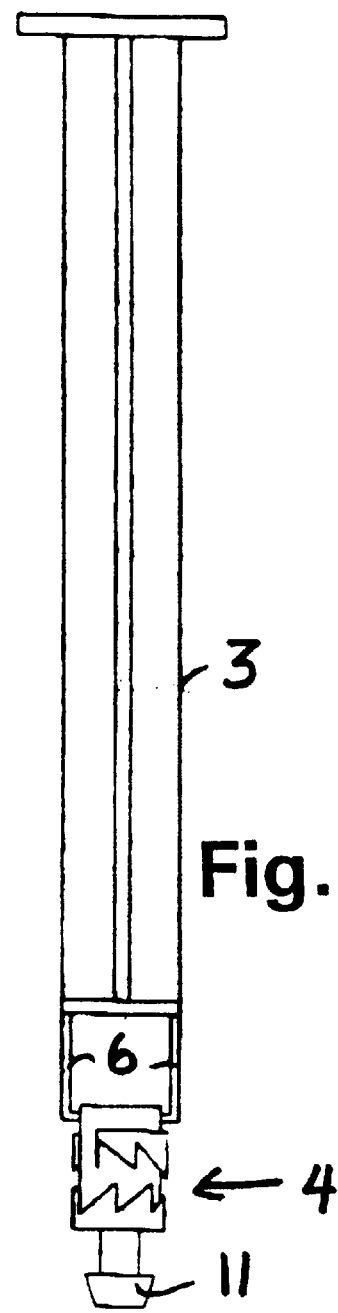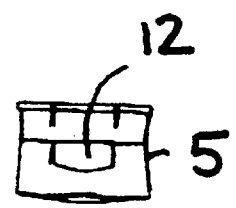
Fig. 1 A
Fig. 1 B
Fig. 1 C

SELF-DESTRUCTING INJECTION SYRINGE

The present application relates to a self-destructing hypodermic syringe comprising an optionally graduated barrel having a Luer lock-tip in one end and a plunger head with plunger rod, of the type having a breaking element incorporated in connection with the plunger or plunger rod, where the breaking element is broken when the syringe is used for the first time.

To be more precise, the invention relates to a syringe wherein there is incorporated a breaking element of this kind which in principle is broken the instant the syringe is put into use.

The principle of the present invention could conceivably be used in several areas, but it is primarily relevant and especially useful in connection with disposable syringes, and the invention and its practical embodiments will therefore be illustrated with the aid of disposable syringes.

Today, such syringes are used extensively by doctors, in hospitals and other health institutions, and also by diabetics or others who need regular injections and who inject themselves. In addition however, syringes are unfortunately used extensively and repeatedly by "mainliners", addicts who take drugs by injection.

Major problems have arisen in connection with the last-mentioned category of users, namely the reuse of syringes, even conventional disposable syringes.

Recently there has been an alarming spread of diseases transmitted by blood because drug addicts lend each other their syringes. Of these infectious diseases special mention can be made of hepatitis B and AIDS.

Self-destructing hypodermic syringes having a breaking member which is broken after the syringe has been used for the first time are known. However, it has been found that the majority of solutions that hitherto have been proposed have either been too expensive to manufacture or have been unsafe to use since it has been possible to manipulate the syringe so that it could be reused.

From the prior art, particular reference will be made to NO 163263 which describes a self-destructing hypodermic syringe of the disposable type, generally of the type described above, wherein the breaking element consists of an element having at least one cam follower which interacts with a cam or a link, extending obliquely relative to the syringe axis, in a second member, which cam or link at its end is connected to an axially extending cam or link that is open towards one end of the member, that a stopper is provided for the cam follower at the end of the cam opposite the connection to the link, and that on the plunger rod or between this and the plunger there is provided a freely rotating member.

The objective of the present invention is to improve the known art and therefore to provide a self-destructing hypodermic syringe of the disposable kind which is both inexpensive to make and safe to use, i.e., that after the first and only use it can no longer be used.

The invention therefore relates to a self-destructing hypodermic syringe of the type mentioned above, and this syringe is characterised by the features set forth in the characterising clause of the main claim.

The mode of operation and the construction of the syringe according to the invention are based on a study of the steps taken today when giving intravenous and intramuscular injections, these steps being laid down by the health authorities and reinforced in the training of health personnel to increase safety in otherwise routine operations.

In principle, the steps of an injection can be summarised as given below, on the basis of a syringe barrel having a needle attached thereto and a plunger, where the plunger rod is inserted halfway:

1) the plunger is pressed to the bottom to express air from the barrel;
2) the needle is inserted through the membrane of a phial and the plunger is drawn back to aspirate the desired volume;
3) the syringe is positioned needle up, the syringe barrel is flicked and the plunger is introduced into the barrel to express any last remaining air, whereupon the needle is inserted into a muscle or blood vessel;
4) the insertion of the needle is checked in that the plunger is drawn out a little;
5) the true injection is carried out and the plunger is pressed to the bottom;
6) the plunger is pulled out to facilitate cleaning, destruction of medicament residue, dismantling, or with the type of syringe discussed here, final destruction of the syringe.

The syringe according to the present invention is, as indicated above, constructed with this work cycle in mind and its mode of operation will be explained in more detail with reference to the accompanying drawings, wherein:

FIG. 1 shows the three original main elements in the syringe according to the invention:

FIG. 1a) the syringe housing with Luer lock-tip,

FIG. 1b) the plunger rod with breaking element, and

FIG. 1c) the plunger head;

Figure 2:
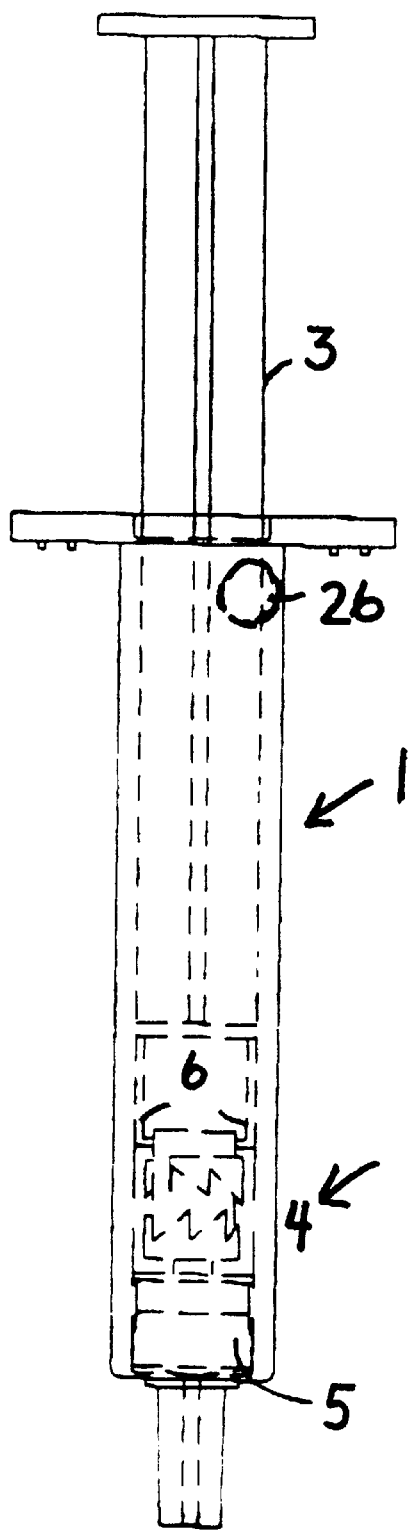
FIG. 2 shows the syringe according to the invention with the plunger in the bottom position but prior to the break.
Figure 3:
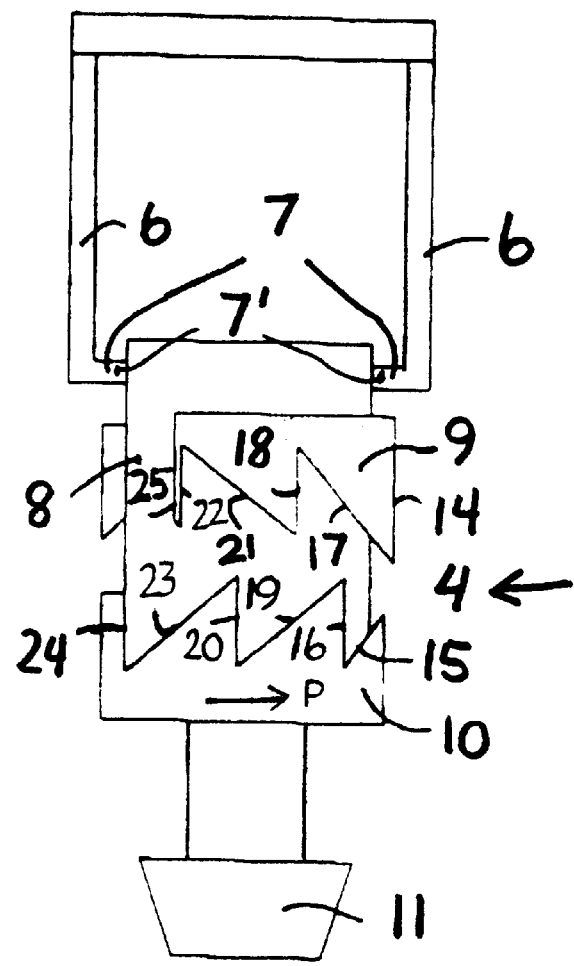
FIG. 3 shows the breaking element with cam follower hoops prior to the break.
Figure 4:
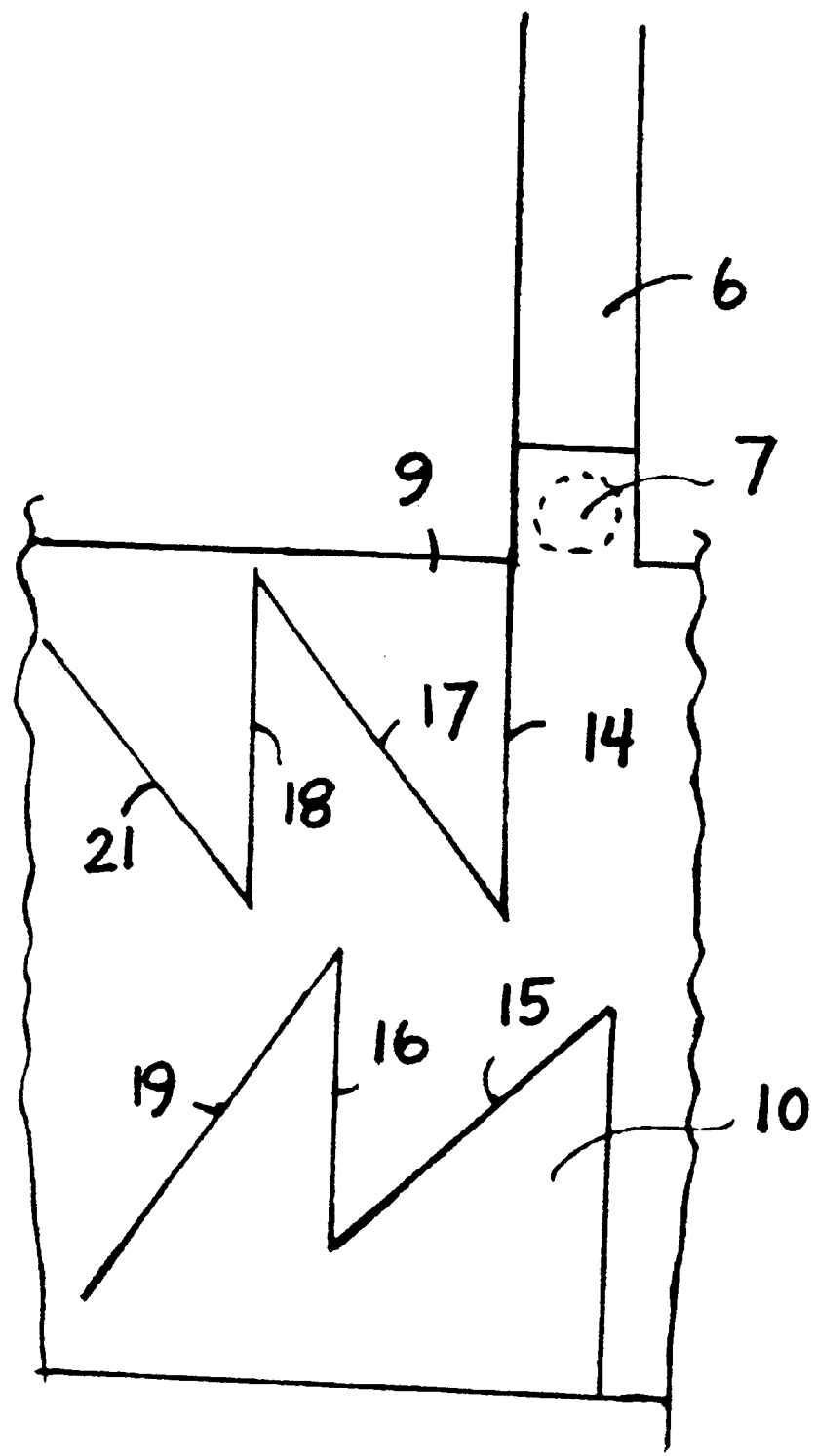
FIG. 4 shows an outline of the breaking element according to FIG. 3, enlarged and turned 90°.

The syringe 1 according to the invention has three main elements, the syringe housing 2, the plunger rod 3 with the breaking element 4, and the plunger head 5.

These parts are shown separately in FIG. 1, and once assembled in FIG. 2.

Furthermore, in FIG. 2 the plunger rod 3 with the breaking element 4 and the plunger head 5 has been run to the bottom in the barrel 2 but not yet loaded to break, as will be explained below.

The following description is based on the procedural sequence as described in the foregoing.

The staff receive the syringe in a condition where the plunger rod 3, the breaking element 4 and the plunger head 5 are mounted halfway inserted in the plunger housing 2.

For connection between the plunger rod 3 via the breaking element 4 and the plunger head 5 and to ensure a rotating connection, the breaking element 4 is equipped with a rotating member 11, whilst the plunger head is equipped with a corresponding rotating bearing 12. This may have the illustrated form, but may also have any other form, e.g., a spherical form, the condition being only that the plunger head 5 is securely attached to the rotating member 11 and that it can rotate freely.

In step 1 of the injection procedure, after affixing a non-illustrated conventional needle on the Luer lock-tip 13, the plunger head 5 with the aid of the plunger rod 3 and via the breaking element 4 is pushed to the bottom of the barrel 2.

Until now the plunger rod 3 and the breaking element 4 have been one unit via cam follower hoops 6, however the connection is broken by load at perforations 7' in the lugs 7, vertically projecting in the direction of the breaking element, on the cam follower hoops 6, and the lugs then become cam followers 7.

According to the invention, when loaded thus, the true destruction of the syringe takes place, but the destruction takes place in such a way that the syringe can still function according to its purpose in order to complete a full injection cycle.

After the break and formation of the cam followers 7, the cam follower hoops and cam followers 7 are pressed downwards so that they grip across the breaking element 4, which in its upper part is fashioned as a cam holder 8 having an upper cam 9 and a lower cam 10.

The cam follower 7, during its downwardly directed movement along the first vertical edge 14 of the cam 9, will meet the first bevelled edge 15 of the cam 10. This forces the breaking element to turn in the direction of the arrow P until the cam follower 7 rests on the bottom between the bevelled edge 15 and the first vertical edge 16 of the lower cam 9. With the plunger in this position, step 2 of the injection procedure is carried out, the needle is inserted through the membrane of a phial and the plunger is pulled back to aspirate the desired volume of injection liquid. On this movement the cam follower 7 will move along the first vertical edge 16 of the lower cam and then meet the first bevelled edge 17 of the upper cam 9, thereby forcing the breaking element to turn again in the direction of the arrow P until the cam follower 7 comes to rest in the angle between the first bevelled edge 17 and the second vertical edge 18 of the upper cam 9.

After said aspiration, the unit is ready for step 3 of the procedure where the syringe is turned so that the needle points up, and usually the syringe barrel is flicked to remove air. The plunger is then introduced into the cylinder again to express the last remaining air, whereupon the needle is inserted into the muscle or blood vessel.

On the expression of air, the cam follower 7 moves along the second vertical edge 18 of the upper cam 9 and comes to rest against the second bevelled edge 19 of the lower cam 10 and forces the breaking element to turn yet again in the direction of the arrow P until the cam follower comes to rest in the angle between the second bevelled edge 19 and the second vertical edge 20 of the lower cam 10.

After the insertion of the needle in step 4 of the injection procedure, this needle insertion is checked in that the plunger is pulled out a little until the first signs of blood appear.

When the plunger is pulled out thus, the cam follower 7 moves along the second vertical edge 20 of the lower cam 10 and comes to rest against the second bevelled edge 21 of the upper cam 9 and forces the breaking element to make a further turn in the direction of the arrow P until the cam follower rests in the angle between the second bevelled edge 21 and the third vertical edge 22 of the upper cam 9.

The true injection now follows in step 5, and the cam follower moves along the third vertical edge 22 of the cam 9 and comes to rest against the third bevelled edge 23 of the lower cam 10, whereby the breaking element is once more turned in the direction of the arrow P until the cam follower comes to rest against the third bevelled edge 23 of the lower cam 10, and the breaking element 4 is turned yet again in the direction of the arrow P until the cam follower rests in the angle between the third bevelled edge 23 and the third vertical edge 24 of the lower cam 10.

Once the injection has been completed, the final, visible destruction is carried out in that the plunger rod with hoops 6 and cam followers 7 is pulled out, thereby allowing the cam followers to freely follow the groove which is formed between the third vertical edge 24 on the lower cam 10 and the fourth vertical edge 25 on the upper cam 9.

The thus destroyed syringe can no longer be used without a manipulating introduction of elements corresponding to the cam follower hoops 6 and the cam followers 7 to bring these, by turning, into engagement, which enables the breaking element 4 with the plunger head 5 to be withdrawn. However, this can be prevented in a very simple manner with the aid of suitable means in connection with the barrel 2, for example, impressing suitable means, such as bosses, indicated by means of the reference numeral 26, which cause a plunger rod 3, suitably fashioned, for example, as a cross, to be prevented from turning in the housing 2.

The syringe according to the invention offers various advantages over the conventional art.

Firstly, it is adapted to the routines which are used today when giving injections, which allows safe and problem-free use.

Secondly, it is simple to manufacture as it is made in three parts, namely the plunger housing 2, the plunger rod 3 with breaking element 4 and the actual plunger head 5.

This allows simplified production since compared to previously known syringes of this type one production stage is saved by the simultaneous casting of the plunger 3 and the breaking element 4.

In an alternative embodiment of the invention, namely where the self-destructing hypodermic syringe is intended for vaccine, a whole "push-pull" step can be omitted as it is not necessary to check that the needle has been inserted correctly.

This means that, for example, the cam top which is formed by the cam edges 16 and 19 on the lower cam and the cam top formed by the cam edges 18 and 21 on the upper cam can be omitted with corresponding smoothing and configuration of the other cam edges.

Thus, the syringe according to the invention represents a considerable advance in relation to the prior art in terms of both safety and production.

I claim:

1. A self-destructing hypodermic syringe (1) comprising an optionally graduated barrel (2) having a Luer lock-tip (13) in one end and a plunger head (5) with plunger rod (3), of the type which has a breaking element (4) incorporated in connection with the plunger head or plunger rod, and where the breaking element (4), initially, prior to destruction, is secured to the plunger rod (3) via diametrically arranged cam follower hoops (6) and lugs (7) which, when loaded, are broken at perforations (7') while converting the lugs (7) to cam followers (7), whereby the breaking element (4) comprises an upper part in the form of a cam holder (8) having an upper cam (9) and a lower cam (10) which defined therebetween a groove for the cam followers (7), wherein the groove, in addition to cam edges (14, 18, 22, 25) on the upper cam and (16, 20, 24) on the lower cam running parallel with the axis of the syringe (1), is defined by obliquely extending cam edges (17, 21) on the upper cam and (15, 19, 23) on the lower cam, where the inclined planes extend in the same peripheral direction from the groove between the cams (9, 10) respectively towards the upper and the lower part of the cam holder (8), the cam tops formed by the syringe-parallel cam edges and the obliquely extending cam edges being displaced relative to one another in such a way that the cam followers (7), when the syringe is used, once they leave a cam, are taken up by an opposite inclined plane and, on further actuation, force the breaking element (4) to turn, the cam followers (7) and the cam follower hoops (6) remaining substantially rotationally stationary while the breaking element (4) is turning (4), whereby the inlet to the cam groove extends along the syringe-parallel edge (14) on the upper cam (9) towards the bevelled edge (15) on the lower cam (10), and the outlet from the groove is found between the extended, syringe-parallel cam edge (24) on the lower cam and a syringe-parallel edge (25) on the upper cam, and a lower part in the form of a rotating member (11) for rotating engagement in a rotating bearing (12) in the plunger head (5), characterised in that the breaking element (4) is cast in one piece with the plunger rod (3) and breaks when the syringe (1) is used for the first time.

* * * * *